(12) United States Patent
Ziemek et al.

(10) Patent No.: US 8,920,475 B1
(45) Date of Patent: Dec. 30, 2014

(54) VERTEBRAL FIXATION SYSTEM INCLUDING TORQUE MITIGATION

(75) Inventors: Terry Ziemek, Broomfield, CO (US); Greg Causey, Erie, CO (US); Michael Fulton, Superior, CO (US)

(73) Assignee: Lanx, Inc., Broomfield, CO (US)

( * ) Notice: Subject to any disclaimer, the term of this patent is extended or adjusted under 35 U.S.C. 154(b) by 184 days.

(21) Appl. No.: 13/345,184

(22) Filed: Jan. 6, 2012

Related U.S. Application Data

(60) Provisional application No. 61/430,875, filed on Jan. 7, 2011.

(51) Int. Cl.
*A61B 17/70* (2006.01)

(52) U.S. Cl.
USPC .......................... 606/267; 606/268

(58) Field of Classification Search
USPC ................................. 606/250–278
See application file for complete search history.

(56) References Cited

U.S. PATENT DOCUMENTS

| | | | |
|---|---|---|---|
| 2,774,350 A | 12/1956 | Cleveland, Jr. | |
| 5,084,049 A | 1/1992 | Asher et al. | |
| 5,257,994 A | 11/1993 | Lin | |
| 5,380,325 A | 1/1995 | Lahille et al. | |
| 5,725,527 A | 3/1998 | Biedermann et al. | |
| 6,264,658 B1 | 7/2001 | Lee et al. | |
| 6,290,703 B1 | 9/2001 | Ganem | |
| 6,443,953 B1 | 9/2002 | Perra et al. | |
| 6,641,583 B2 * | 11/2003 | Shluzas et al. ................ | 606/252 |
| 7,306,603 B2 | 12/2007 | Boehm, Jr. et al. | |
| 7,569,068 B2 | 8/2009 | Ramare | |
| 7,628,799 B2 | 12/2009 | Richelsoph et al. | |
| 7,645,294 B2 | 1/2010 | Kalfas et al. | |
| 7,666,210 B2 | 2/2010 | Franck et al. | |
| 7,727,259 B2 | 6/2010 | Park | |
| 7,744,635 B2 | 6/2010 | Sweeney et al. | |
| 7,794,500 B2 | 9/2010 | Felix | |
| 7,833,251 B1 | 11/2010 | Ahlgren et al. | |
| 7,875,031 B2 | 1/2011 | Chin et al. | |
| 7,879,074 B2 | 2/2011 | Kwak et al. | |
| 7,927,355 B2 | 4/2011 | Berrevoets et al. | |
| 8,523,911 B2 * | 9/2013 | Jani et al. ................ | 606/250 |
| 2003/0216737 A1 * | 11/2003 | Biscup ............................ | 606/61 |
| 2004/0158247 A1 | 8/2004 | Sitiso et al. | |
| 2005/0080420 A1 | 4/2005 | Farris et al. | |
| 2005/0228326 A1 * | 10/2005 | Kalfas et al. .................... | 602/19 |
| 2006/0052783 A1 * | 3/2006 | Dant et al. ....................... | 606/61 |
| 2007/0118121 A1 | 5/2007 | Purcell et al. | |
| 2007/0173800 A1 | 7/2007 | Sanders et al. | |
| 2008/0177327 A1 | 7/2008 | Malandain et al. | |
| 2009/0088799 A1 | 4/2009 | Yeh | |
| 2009/0105755 A1 * | 4/2009 | Capote .......................... | 606/246 |
| 2009/0318968 A1 * | 12/2009 | Duggal et al. ................ | 606/250 |
| 2009/0318969 A1 | 12/2009 | Matthis et al. | |

(Continued)

FOREIGN PATENT DOCUMENTS

| | | |
|---|---|---|
| WO | 2010010259 A1 | 1/2010 |
| WO | 2011012829 A2 | 2/2011 |

*Primary Examiner* — Mary Hoffman
*Assistant Examiner* — Tara Carter
(74) *Attorney, Agent, or Firm* — Harness, Dickey

(57) ABSTRACT

Various spinal fixation assemblies are presented that include a separator installable in relation to a coupler attached to the head of an anchor device, and disposable between the head of the anchor device and a cross member. The separators may be implemented in a variety of forms.

10 Claims, 8 Drawing Sheets

(56) References Cited

U.S. PATENT DOCUMENTS

| | | |
|---|---|---|
| 2010/0016898 A1 | 1/2010 | Shluzas |
| 2010/0087861 A1 | 4/2010 | Lechmann et al. |
| 2010/0160981 A1 | 6/2010 | Butler et al. |
| 2010/0174315 A1 | 7/2010 | Scodary et al. |
| 2010/0198259 A1 | 8/2010 | Drewry et al. |
| 2010/0198269 A1 | 8/2010 | Taylor et al. |
| 2010/0228292 A1 | 9/2010 | Arnold et al. |
| 2010/0274285 A1 | 10/2010 | Rouleau |
| 2011/0046675 A1 | 2/2011 | Barrus et al. |
| 2011/0066187 A1 | 3/2011 | Fang et al. |

* cited by examiner

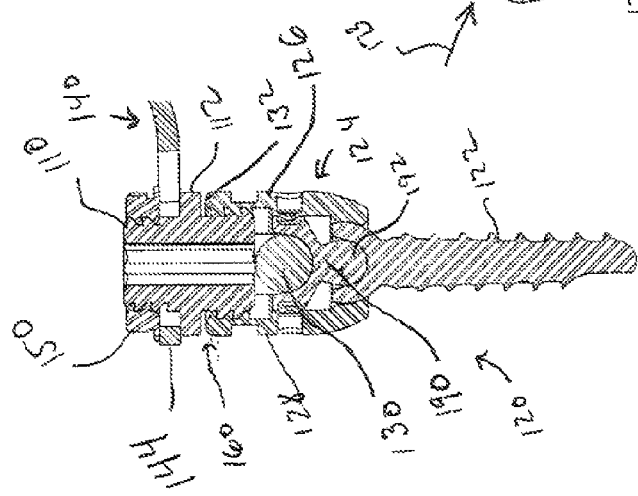
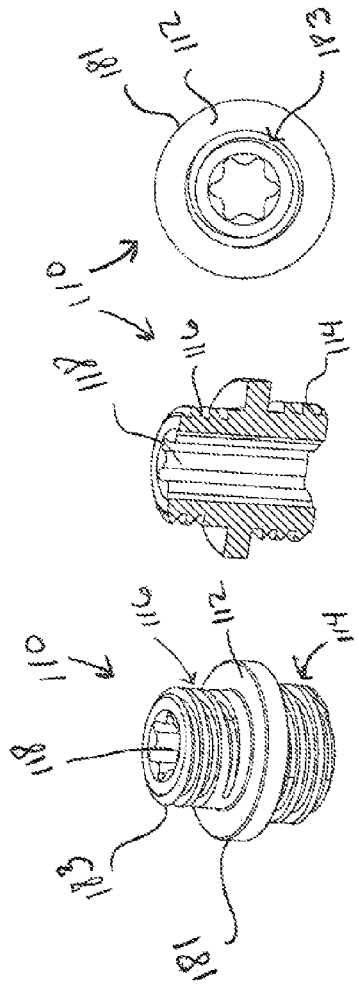
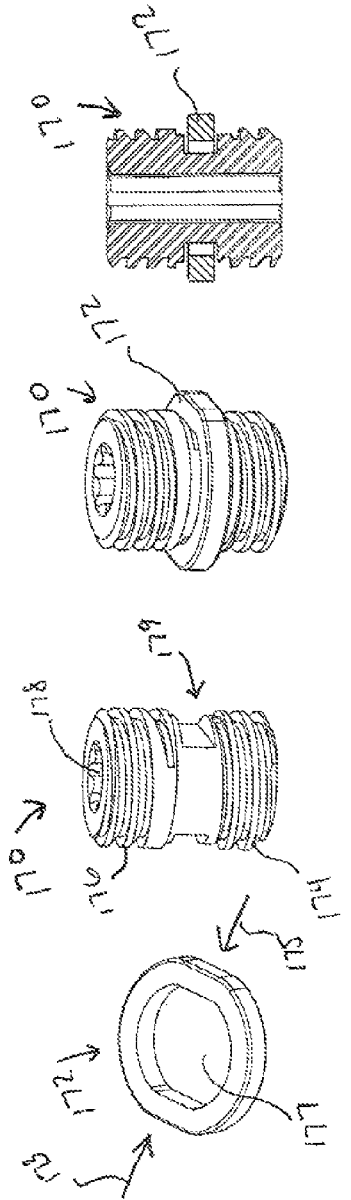

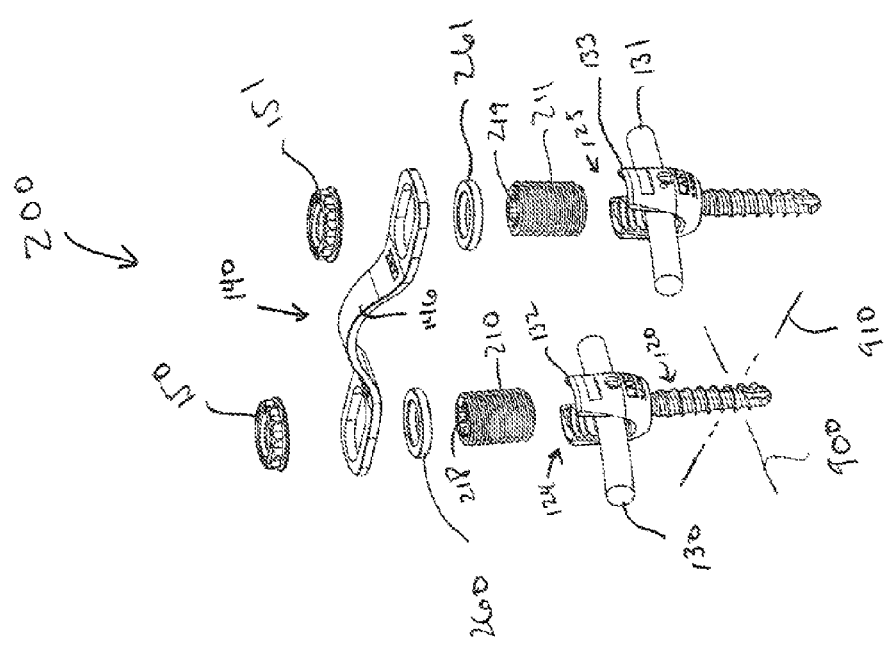

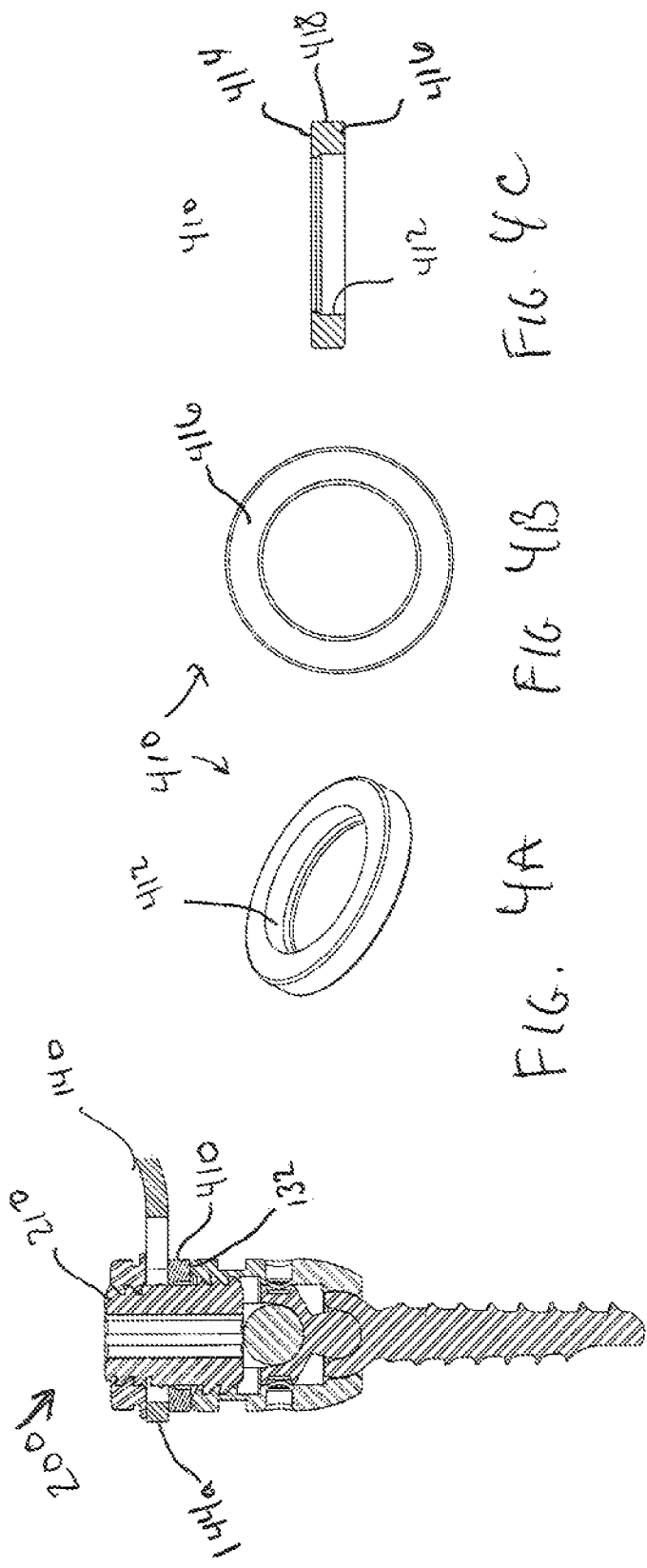

VERTEBRAL FIXATION SYSTEM INCLUDING TORQUE MITIGATION

RELATED APPLICATIONS

The present application claims priority from U.S. Provisional Patent Application No. 61/430,875 entitled "Vertebral Fixation System Including Torque Mitigation" by: Ziemek et al., filed on Jan. 7, 2011, which Provisional Patent Application is hereby incorporated by reference in its entirety.

BACKGROUND

The present disclosure sets forth various implantable medical devices, and more particularly, various vertebral fixation systems and methods for using such are described herein.

Back pain may be caused where one or more intervertebral discs degenerate resulting in pressure on the nerves protected by the spine. In some cases, to relieve pressure on the nerves, vertebrae on either side of a problem intervertebral disc are fused together. Fusing the vertebrae typically includes fixing the opposing vertebrae such that the fixed vertebrae cannot move relative to one another. By fixing the vertebrae relative to each other, the region between the vertebrae ossifies resulting in the desired fusion.

Fixing vertebrae to one another may involve installing pedicle screws into the vertebrae, and subsequently installing rods between the pedicle screws to help limit any movement of the vertebrae relative to one another. In some cases, the installation process is a multi-step process with one step of the process potentially acting to partially undo an earlier process. For example, screws that are inserted into bone may loosen if excessive torque or other forces are later applied to the screw construct. Such is undesirable and may reduce the long term stability of the installed elements.

Hence, for at least the aforementioned reasons, there exists a need in the art for advanced systems and methods for fixing one vertebra relative to another.

BRIEF SUMMARY

The present disclosure sets forth various implantable medical devices, and more particularly, various vertebral fixation systems and methods for using such are described herein.

Various embodiments of vertebral fixation systems are disclosed that include an anchor device, a coupler, a cross member and a separator. The anchor device includes a head with an upper edge. One end of the coupler is configured for attaching to the head, and another end of the coupler is configured for attaching to a fastener. The cross member is configured for securing by the coupler between the head and the fastener, and the separator is disposable between the upper edge of the head and the cross member. In some cases, the anchor device is a pedicle screw. In particular cases, the coupler is a set screw having screw threads, the fastener is a nut having nut threads configured to engage the screw threads, and the head has an opening defined by opposing head sides separated by a negative space. The head sides have head threads configured to engage the screw threads. In various cases, at least a portion of a surface of the cross member is roughened. This roughened surface may contact one or both of the fastener and the separator when the system is assembled.

In some instances of the aforementioned embodiments, the separator and coupler are formed as a single part. In some such instances, a rod member is secured in the head. In such instances, the head has a head seat defined by a first head side separated from a second head side by a negative space. The rod member is configured for placement in the head seat and is secured in place by the coupler. With the rod member secured in place, a gap exists between the separator and the upper edge of the head.

In various instances of the aforementioned embodiments, the coupler includes a threaded surface, and the separator is a nut that is configured to engage the threaded surface. In some such instances, the fastener is also a nut that is configured to engage the threaded surface. When installed, the nut acting as the separator contacts the upper edge of the head.

In yet other instances of the aforementioned embodiments, the separator is a washer that is configured to slide over the coupler. In some such instances, when the system is assembled, an outer edge of the washer extends a greater distance from an outer edged of the coupler than the head extends from the surface of the coupler such that the washer overhangs the head. In various cases, the washer contacts the upper edge of the head when the fastener is attached to the coupler.

In one or more instances of the aforementioned embodiments, the head has a head seat defined by a first head side separated from a second head side by a first negative space and second negative space. In such instances, the separator may include a first separator side configured to extend into the first negative space between the first head side and the second head side, and a second separator side configured to extend into the second negative space between the first head side and the second head side. The aforementioned separator may be lockable to the coupler. In some cases, the head seat is configured to receive a rod member. In such cases, the first separator side and the second separator side contact the rod member when the fastener is attached to the coupler. In particular cases, contact between the separator sides and the rod member results in a gap between the separator and the upper edge of the head when the fastener is installed.

In various cases, the separator includes spaced apart first and second legs coupled to a ring member. The first and second legs are configured to engage the rod member when the separator is coupled to the coupler. The ring member is disposable between the cross member and the upper edge of the head. In particular cases, contact between the first and second legs and the rod member results in a gap between the ring member and the upper edge of the head when the fastener is installed.

Other disclosed embodiments provide methods for vertebral fixation. Such methods employ a vertebral fixation system that includes, but is not limited to, two anchor devices that each include a head, two couplers, two fasteners, a cross member, two rod members, and two separators. The methods include: securing the two anchor devices to a vertebra; installing one of the rod members into the head of one of the anchor devices and another of the rod members into the head of the other anchor device; attaching one of the couplers to the head of one of the anchor devices and the other coupler to the head of the other anchor device such that the previously installed rod members are secured; attaching the cross member between the couplers such that one of the separators is disposed between the cross member and the head of one of the anchor devices, and the other separator is disposed between the cross member and the head of the other anchor device; and attaching one of the fasteners to one of the couplers and the other fastener to the other coupler such that the cross member is secured between the couplers.

Yet other disclosed embodiments provide vertebral fixation kits. Such kits include a plurality of anchor devices; a plurality of couplers; a plurality of rod members, a plurality of cross members; and a plurality of separators. Each of the anchor devices has a head, and each of the plurality of couplers has a first end that is configured to attach to the head of each of the plurality of anchor devices. A second end of each of the couplers is configured for attaching to a fastener. Each of the plurality of cross members is configured for securing between two of the plurality of couplers, each of the plurality of rod members is configured for securing to an anchor device, and each of the plurality of separators is disposable between a head of one of the plurality of anchor devices and one of the plurality of cross members. In some cases, the plurality of anchor devices include pedicle screws; the plurality of couplers include set screws having screw threads that are configured to engage the heads of the plurality of anchor devices; the separators include washers that are configured to slide over the couplers; and the fastener is a nut having nut threads configured to engage the screw threads.

This summary provides only a general outline of some embodiments disclosed herein. Many other objects, features, advantages and other possible modifications to the disclosed embodiments will become more fully apparent from the following detailed description, the appended claims and the accompanying drawings.

BRIEF DESCRIPTION OF THE DRAWINGS

A further understanding of the various embodiments of the present disclosure may be realized by reference to the figures which are described in remaining portions of the specification. In the figures, like reference numerals are used throughout several drawings to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

FIG. 1B is a cross-sectional view of one leg of the vertebral fixation assembly of FIG. 1A after assembly;

FIG. 1C-1E are respectively perspective, cross-sectional side and top views of the set screw and separator combination of FIG. 1A;

FIGS. 1F and 1G depict a separate set screw and washer that can be formed into a single part combination set screw and separator;

FIGS. 1H and 1J show cross-sectional and perspective views, respectively, of the washer of FIG. 1G installed on the set screw of FIG. 1F;

FIG. 2 is an exploded perspective view of a vertebral fixation assembly including a separator distinct from a coupler in accordance with some embodiments;

FIGS. 4A-4C respectively show perspective, top plan, and cross-sectional side views of a washer that may be used as the separator in the vertebral fixation assembly of FIG. 2 in accordance with some embodiments;

FIG. 4D is a cross-sectional view of one leg of the vertebral fixation assembly of FIG. 2 after assembly using the washer of FIGS. 4A-4C as the separator;

DETAILED DESCRIPTION

Figure 1A:
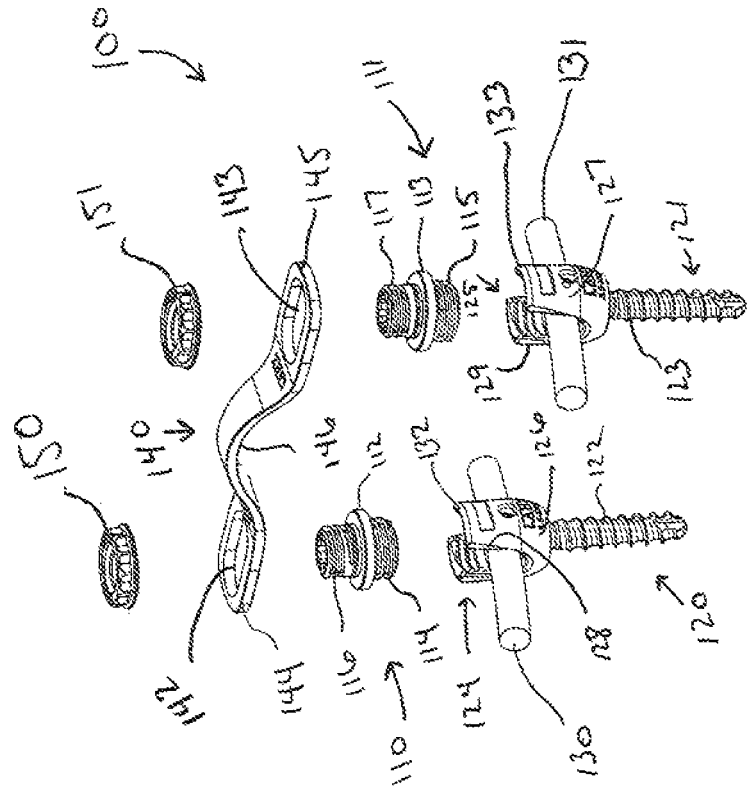
FIGS. 1 and 1A are a perspective view and an exploded perspective view, respectively, of a vertebral fixation assembly including a set screw and separator formed together as a single part in accordance with various embodiments.
Figure 1:
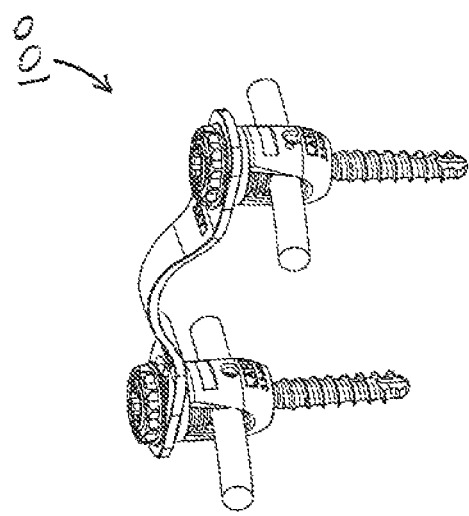

The present disclosure sets forth various implantable medical devices, and more particularly, various vertebral fixation systems and methods for using such are described herein.

Vertebral fixation systems may be used to fix one vertebra to another vertebra, as part of a spinal fusion or other surgical procedure. Vertebral fixation systems may include anchor devices that are installed into adjacent vertebrae. In some embodiments, the anchor devices are pedicle screws, and are used to anchor or couples rods which extend vertically across one or more disc segments. Depending on a variety of factors, including without limitation, the rod length and type, some fixation systems also include cross members which couple laterally between two rods or pedicle screws. In this manner, a single rod may be coupled to two or more anchor devices, and also may be coupled to a second rod. In some situations, the cross members cannot connect directly to rods. This may occur, for example, when two anchor devices are close together and the rod running between them does not provide sufficient room to connect a cross member. In such a situation, as well as others, it may be desirable to connect cross members laterally between two anchor devices.

Securing the cross members may involve application of a torsional force to the cross member, anchor devices and/or rods. Alternatively, or in addition, the cross members may act as lever arms potentially applying torsional force to the previously installed anchor devices during installation of the vertebral fixation system. In either case, applying torsional force to an already installed anchor device has the potential of loosening the anchor device or otherwise undermining the integrity of the vertebral fixation system. Various disclosed embodiments use a separator between an anchor device and one or more other elements of the vertebral fixation system to help reduce the transfer of torsional forces applied during installation of the one or more other elements to the previously installed anchor device.

In some cases, installing a separator between an upper edge of the anchor device and the cross member provides a relatively large surface to which the cross member may be secured. For example, the separator may include a relatively wide surface in contact with the cross member when compared with the available surface of the head of the anchor device. As another example, the separator may offer a three hundred, sixty degree surface area around the coupler in comparison with the head of the anchor device that may include less than three hundred, sixty degree surface area where openings in the head are included to accept a rod member. Such a large surface can reduce the possibility that an installed vertebral fixation system disassembles after deployment.

In various cases, a separator is installed between the cross member and the head of an anchor device that includes side offsets. The side offsets extend down to contact a rod installed in the head of the anchor device, leaving a gap between the head of the anchor device and the separator. By leaving a gap between the separator and the head of the anchor device, transfer of torsional forces due to the contact between a surface of the separator and the surface of the head of the anchor device is limited. Rather, the torsional force is transferred from the separator to the rod member. Where there is some play between the lateral movement of the rod member and the head of the anchor device, transfer of torsional force capable of undermining the installation of the anchor device is limited.

Embodiments of a vertebral fixation system disclosed herein include one or more anchor devices, one or more couplers, one or more cross members, and one or more separators. The anchor devices are used for anchoring the vertebral fixation system to one or more vertebrae or other suitable skeletal structure. As used herein, the phrase "anchor device" is use in its broadest sense to mean any device capable of securing elements to a desired point. Thus, an anchor device may be, but is not limited to, a monoaxial bone screw, a polyaxial bone screw, a bolt, or a hook. As a particular example, the anchor device may be a pedicle screw. Based upon the disclosure provided herein, one of ordinary skill in the art will appreciate a variety of anchor devices that may be used in relation to different embodiments. The elements of the vertebral fixation system may be made of any material suitable for implantation into a body. The materials that may be used include, but are not limited to, titanium and stainless steel.

The couplers are each attachable to the head of a respective anchor device, and provide a mechanism for securing one of more cross members that extend between anchor devices. As used herein, the term "coupler" is used in its broadest sense to mean any member that is capable of connecting one element to another. As an example, a coupler may be used to attach an anchor device to a fastener such that various elements of the vertebral fixation system are secured in place. As a particular example, the couplers may be set screws that are threaded to engage threads in the head of an anchor device and the threads in a fastener. Based upon the disclosure provided herein, one of ordinary skill in the art will appreciate a variety of couplers that may be used in relation to different embodiments. In some cases, when installed the coupler holds a rod member in place relative to the anchor device. As used herein, the phrase "rod member" is used in its broadest sense to mean a structural support that extends between an anchor device and another attachment point. Thus, for example, a rod member may be a rounded length of titanium, cobalt chrome, stainless steel, or a biocompatible plastic such as, for example, PEEK. As another example, a rod member may be a rectangular length of titanium or stainless steel. Based upon the disclosure provided herein, one of ordinary skill in the art will recognize a variety of shapes and dimensions of rod members that may be used in relation to different embodiments.

A cross member and separator are maintained in place by the coupler. The separator is disposed between the head of an anchor device and the cross member. As used herein, the phrase "cross member" is used in its broadest sense to mean a structural support that extends between an anchor device and another fixed point. Thus, a cross member may be, but is not limited to, a rounded rod, a flat or square bar, or a plate of various shapes having openings on either end. Based upon the disclosure provided herein, one of ordinary skill in the art will appreciate a variety of cross members that may be used in relation to different embodiments. The cross member is maintained in place on the coupler by a fastener. As used herein, the term "fastener" is used in its broadest sense to mean any device capable of secure attachment to another device. As an example, a fastener may be a nut with threads designed to engage threads of a coupler. Based upon the disclosure provided herein, one of ordinary skill in the art will recognize a variety of fasteners that may be used in relation to different embodiments.

Contact between a cross member and the head of an anchor device is limited by a separator secured in place by the coupler between the head and the cross member. As used herein, the term "separator" is used in its broadest sense to mean any member that limits the contact between two other members. Thus, for example, a separator may be a washer, a nut, or the like. Based upon the disclosure provided herein, one of ordinary skill in the art will recognize a variety of separators that may be used in relation to different embodiments.

Turning to FIG. 1A, an exploded perspective view of a vertebral fixation assembly 100 will be described. Vertebral fixation assembly 100 includes pedicle screws 120, 121, rod members 130, 131, set screws 110, 111 each with a respective integrated separator 112, 113, a cross member 140, and nuts 150, 151. Pedicle screw 120 includes a shaft 122 and a head 124, and pedicle screw 121 includes a shaft 123 and a head 125. Shafts 122, 123 are each configured for securing to a bone structure such as a vertebra. Head 124 has two opposing sides 126, 128 with negative space between sides 126, 128. The combination of opposing sides 126, 128 and the intervening negative space creates a generally "U" shaped region that provides a seat into which rod member 130 may be removably placed. Rod member 130 is placed in the negative space, and extends out of the gap or negative space between sides 126, 128. Rod member 130 may be, but is not limited to, a rod that extends from pedicle screw 120 installed in one vertebra (not shown) to another pedicle screw (not shown) that is installed in another superior or inferior vertebra (not shown), thereby fixing the vertebrae relative to each other. Similarly, head 125 has two has two opposing sides 127, 129 with negative space between sides 127, 129. The combination of opposing sides 127, 129 and the intervening negative space creates a generally "U" shaped region that provides a seat into which rod member 131 may be removably placed. Rod member 131 is placed in the negative space, and extends out of the gap or negative space between sides 127, 129. Rod member 131 may be, but is not limited to, a rod that extends from pedicle screw 121 installed in one vertebra (not shown) to another pedicle screw (not shown) that is installed in another superior or inferior vertebra (not shown), thereby fixing the vertebrae relative to each other. In some embodiments, pedicle screws 120, 121 are multi-axial screws, each with a head coupled to a shaft in a manner which allows multi-axial movement of the head relative to the shaft. For example, in some embodiments, a seat member 190 is provided within head 124, 125 to receive rod member 130, 131. Seat 190 may include, for example, an extension portion 192 which sits within a corresponding detent in the pedicle screw at the top of shaft 122, 123. In this manner, seat 190 helps provide polyaxial movement between seat 190 and shaft 122, 123. Other mechanisms for providing polyaxial movement are possible.

Set screw 110 includes a lower threaded region 114 separated from an upper threaded region 116 by separator 112; and set screw 111 includes a lower threaded region 115 separated from an upper threaded region 117 by separator 113. FIGS. 1C-1E are perspective, cross-sectional side and top views of set screw 110. It should be noted that set screw 111 is the same as set screw 110, and thus corresponding detailed drawings of set screw 111 are not provided. In this embodiment, separator 112 and set screw 110 are formed as a single part. Formation as a single part may be achieved by, but is not limited to, casting the combination set screw and separator as a single molded piece; machining the combination set screw and separator from a single piece of material; or attaching the separator to the set screw such that they become a single part. FIGS. 1C through 1D depict a set screw machined from a single piece of material. An outer edge 181 of separator 112 extends a distance from an outer edge 183 (i.e., the threads of either or both of lower threaded region 114 and upper threaded region 116) sufficient to stop cross member 140 from touching an upper edge 132 of head 124. An inner surface of both sides 126, 128 of head 124 are threaded to engage the threads of lower threaded region 114; and an inner surface of both sides 127, 129 of head 125 are threaded to engage the threads of lower threaded region 115. As such, set screw 110 can be threadably attached to head 124, and set screw 111 can be threadably attached to head 125. Set screw 110 extends into head 124 a sufficient distance to engage rod member 130 (e.g., contact rod member 130 or an additional component which contacts rod member 130). Once tightened, set screw 110 secures rod member 130 to head 124. In some embodiments, a gap 160 exists between separator 112 and upper edge 132 when set screw 110 is coupled to head 124. Similarly, set screw 111 extends into head 125 a sufficient distance to engage rod member 131 (e.g., contact rod member 131 or an additional component which contacts rod member 131). Once tightened, set screw 111 secures rod member 131 to head 125. In some embodiments, a gap (not shown) exists between separator 113 and upper edge 133 when set screw 111 is coupled to head 125. Set screws 110, 111 each include a patterned inner region 118 configured to interface with a tool (not shown) that is capable of rotating or otherwise engaging set screws 110, 111 into respective heads 124, 125. In some embodiments, patterned inner region 118 is a Torx pattern for receipt of a Torx-headed screwdriver.

FIGS. 1F through 1G show the component parts of a combination set screw and separator that can be assembled such that the component parts become a single part. In particular, FIG. 1F shows a set screw portion 170 having a lower threaded region 174, an upper threaded region 176, and a center region 179. In addition, set screw portion 170 includes a patterned inner region 178 that is configured to interface with a tool (not shown) that is capable of rotating or otherwise engaging set screws 110, 111 into respective heads 124, 125. FIG. 1G shows a deformable washer 172 prior to deformation. Washer 172 has an opening 177 that is substantially circular or other shape, and of a size capable of sliding over at least one end of set screw portion 170 until it is aligned with center region 179. Once aligned with center region 179, an inward directed force is applied to deformable washer 172 as indicated by arrows 173 and 175. This force causes opening 177 to deform such that deformable washer 172 can no longer slide over upper threaded region 176 or lower threaded region 174. As such, deformable washer 172 is secured to set screw portion 170 near or at center region 179, and set screw portion 170 and deformable washer 172 operate as a single part. FIGS. 1J and 1H are perspective and cross-sectional views of the combination of set screw portion 170 and deformable washer 172, with deformable washer aligned with center region 179 and deformed such that opening 177 is no longer able to slide over upper threaded region 176 or lower threaded region 174. It should be noted that deformable washer 172 is only one example of a separator that can be attached to set screw portion 170. Based upon the disclosure provided herein, one of ordinary skill in the art will recognize a variety of other separators and corresponding set screw portions including, but not limited to, a split washer, a split ring, a stake, pins, threads, or the like.

Cross member 140 has two opposing ends 144, 145 on either end of a span 146. Each end 144 includes an opening 142 that is configured to slide over upper threaded region 116, but not over separator 112. As shown, cross member 140 extends between two couplers (i.e., between two pedicle screws each attached to couplers) and thereby generally fixes the distance between the couplers. In some cases, both of openings 142, 143 are circular openings such that the distance required between couplers is not substantially variable. In other cases, one or both of openings 142, 143 are elongated openings such as an oblong opening or a rectangular opening that allow for a range of distances between couplers to be accommodated. This variability is removed once cross member 140 is finally locked in place by threadably attaching and tightening nuts 150, 151 to the respective couplers 110, 111. Based upon the disclosure provided herein, one of ordinary skill in the art will recognize other opening shapes that may be used in relation to different embodiments. Span 146 may be configured in a variety of ways. For example, span 146 may be planar in some embodiments and curved in other embodiments. The curvature may be designed to accommodate any anatomy existing between opposite lateral sides of a vertebra in which pedicle screw 120 and pedicle screw 121 are installed. Additionally, the cross section of span 146 may vary from that depicted in the figures, and span 146 may have a rectangular, circular, oval, or other regular or irregular shaped cross section along some or all of span 146. Based upon the disclosure provided herein, one of ordinary skill in the art will recognize a variety of span shapes that may be used in relation to different embodiments.

FIG. 1B is a cross-sectional view of one assembled leg of the vertebral fixation assembly of FIG. 1A. As shown, when assembled, end 144 of cross member 140 contacts separator 112 that is integrated with coupler 110. Nut 150 is tightened to hold cross member 140 in place against separator 112. Of note, when coupler 110 is threadably attached to head 124 such that it secures rod member 130 in head 124, gap 160 exists between separator 112 and upper edge 132 of head 124. As such, the transfer of any torsional force applied in securing nut 150 to coupler 110 is reduced due to gap 160. Further, the surface area of separator 112 can be greater than that of upper edge 132 of head 124. For example, upper edge 132 includes negative space to accommodate the placement of rod 130 into head 124. In contrast, separator 112 may provide up to three hundred and sixty degrees of contact surface extending around coupler 110. In addition, separator 112 may provide more support for end 144 when compared with upper edge 132 as the width of separator (i.e., the area extending out from set screw 110) may be greater than that of upper edge 132 of head 124. This increase in support may be more significant where opening 142 is an elongated hole.

Turning to FIG. 2, an exploded perspective view of a vertebral fixation assembly 200 will be described, Vertebral fixation assembly 200 includes pedicle screws 120, 121, rod members 130, 131, set screws 210, 211, separators 260, 261, a cross member 140, and nuts 150, 151. In contrast to vertebral fixation assembly 100 of FIG. 1A, the set screws are not incorporated with a separator, but rather, set screw 210 is a distinct part from separator 260 and set screw 211 is a distinct part from separator 261. In the depicted embodiment, set screws 210, 211 each include a continuous threaded surface over which separators 260, 261 may be placed.

Figure 3:
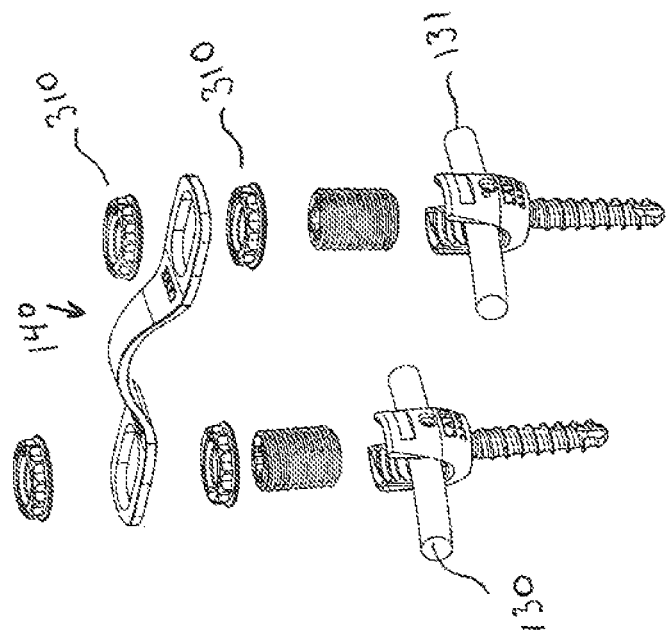
FIGS. 3 and 3E are an exploded perspective view and a perspective view, respectively, of a vertebral fixation assembly including a set screw and separator in accordance with various embodiments.
Figure 3E:
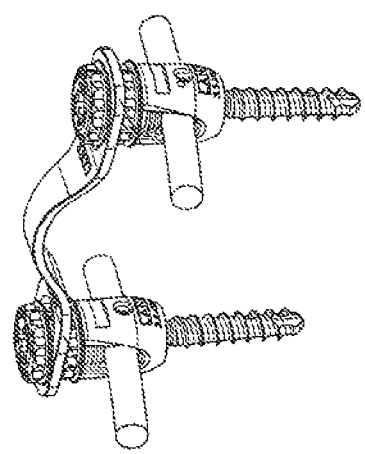

When assembled, set screw 210 is threadably attached into head 124 such that it contacts or otherwise engages rod member 130 and secures rod member 130 in place. Similarly, set screw 211 is threadably attached into head 125 such that it contacts or otherwise engages cross member 131 and secures cross member 131 in place. Set screw 210 includes a patterned opening 218, and set screw 211 includes a patterned opening 219. Patterned openings 218, 219 are configured such that a tool (not shown) can be inserted and a torsional force applied to the set screw to tighten it into the respective head 124. As more fully detailed in relation to FIGS. 3-5, separators 260 are installed relative to the respective set screws 210, 211 such that separators 260, 261 are disposed between heads 124, 125 and cross member 140. Openings 142, 143 in cross member 140 are then slid over respective set screws 210, 211 until ends 144, 145 rest on respective separators 260, 261. Cross member 140 is then secured in place by threadably attaching nut 150 onto set screw 210 such that end 144 is are secured between nut 150 and separator 260, and nut 151 is threadably attached onto set screw 211 such that end 145 is secured between nut 151 and separator 261.

Figure 3C:
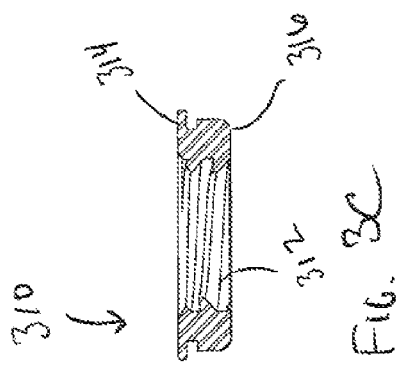
FIGS. 3A-3C respectively show perspective, top plan, and cross-sectional side views of a nut that may be used as the separator in the vertebral fixation assembly of FIG. 2 in accordance with various embodiments.
Figures 3A, 3B:
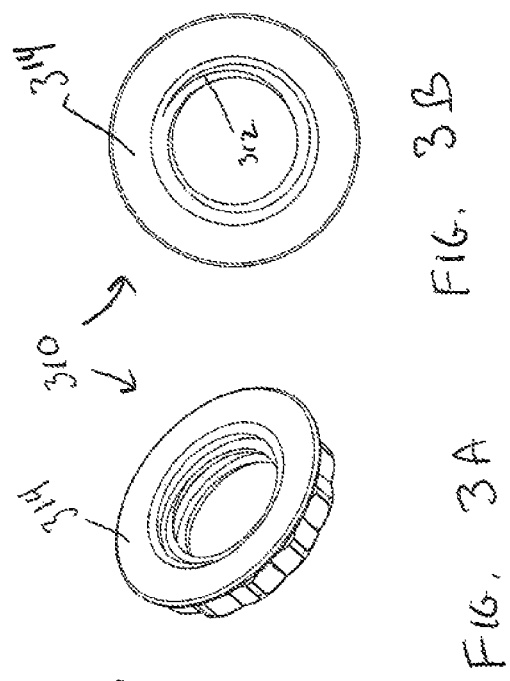
Figure 3D:
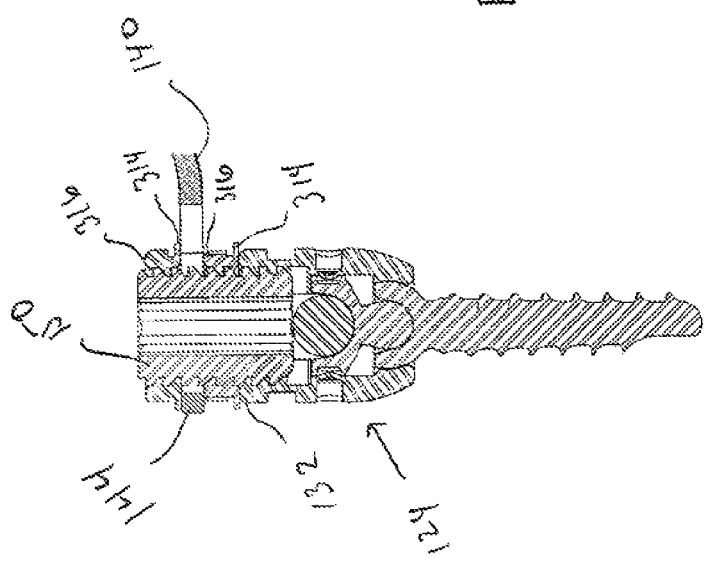
FIG. 3D is a cross-sectional view of one leg of the vertebral fixation assembly of FIG. 2 after assembly using the nut of FIGS. 3A-3C as the separator.

Different embodiments may use different types of separators 260, 261 including, but not limited to, nuts, washers or side offset separators. FIGS. 3A-3C respectively show perspective, top, and cross-sectional side views of a nut 310 that may be used as separators 260, 261. Nut 310 includes a threaded inner surface 312 that is configured to interface with the threads on the outer surface of set screws 210, 211, an upper surface 316, a lower surface 314, and an outside edge 318 that may be configured for gripping by a tool (not shown) for tightening and loosing nut 310 on set screws 210, 211. FIG. 3D is a cross-sectional view of one leg of the vertebral fixation assembly 200 of FIG. 2 after assembly where nut 310 is used as separator 260. As shown, end 144 of cross member 140 is pressed against upper surface 316 of nut 310, and lower surface 314 of nut 310 is pressed against upper edge 132 of head 124 when nut 150 is tightened. In some cases, upper surface 316 may be roughened to increase the amount of friction between upper surface 316 and cross member 140, and/or lower surface 314 and/or upper edge 132 of head 124 may be roughened to increase friction. Similar roughening may be applied to ends 144, 145 of cross member 140, upper edge 132 of head 124, upper edge 133 of head 125, and/or the lower surface of nuts 150, 151. Such roughening may be achieved by abrading or sandblasting the surface(s) of nuts 310, nuts 150, 151, and/or ends 144, 145 of cross member 140. Based upon the disclosure provided herein one of ordinary skill in the art will recognize a variety of processes that may be employed to roughen the respective surfaces.

FIGS. 4A-4C respectively show perspective, top, and cross-sectional side views of a washer 410 that may be used as separators 260, 261. Washer 410 includes a non-threaded inner surface 412 of a size that allows washer 410 to slide over the outer surface of set screw 210, an upper surface 416, a lower surface 414, and an outside edge 418. FIG. 4D is a cross-sectional view of one leg of the vertebral fixation assembly 200 of FIG. 2 after assembly where washer 410 is used as separator 260. As shown, end 144a of cross member 140 is pressed against upper surface 416 of washer 410, and lower surface 414 of washer 410 is pressed against upper edge 132 of head 124 when nut 150a is tightened. In some cases, upper surface 416 and/or lower surface 414 may be roughened to increase the amount of friction between upper surface 416 and cross member 140, and/or lower surface 414 and upper edge 132 of head 124. Similar roughening may be applied to ends 144, 145 of cross member 140, upper edge 132 of head 124, upper edge 133 of head 125, and/or the lower surface of nuts 150, 151. Such roughening may be achieved by abrading or sandblasting the surface(s) of washers 410, nuts 150, 151, upper edge 132 of head 124, upper edge 133 of head 125, and/or ends 144, 145 of cross member 140. Based upon the disclosure provided herein one of ordinary skill in the art will recognize a variety of processes that may be employed to roughen the respective surfaces.

Figure 5B:
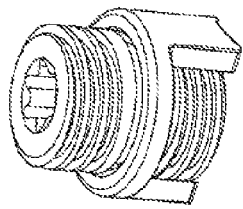
FIGS. 5B-5C respectively show perspective and perspective, cross-sectional views of the side offset separator of FIG. 5A disposed in relation to a set screw.
Figure 5F:
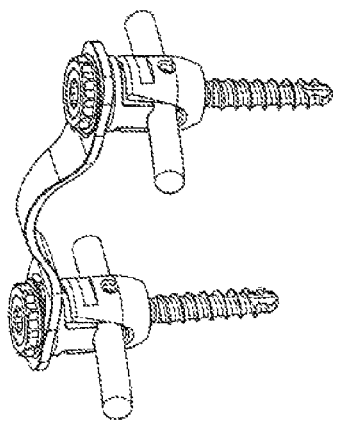
FIG. 5F is a perspective view of the vertebral fixation assembly using the side offset separator of FIG. 5A as the separator.
Figures 5A, 5C:
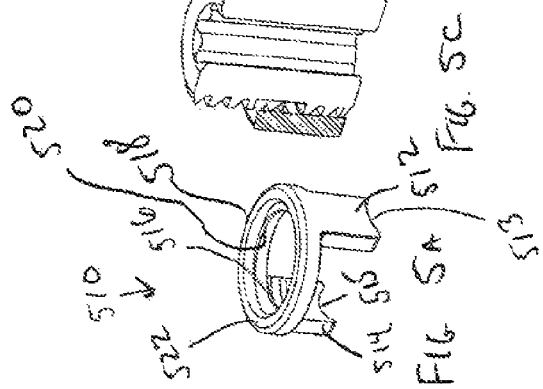
FIG. 5A is a perspective view of a side offset separator that may be used as the separator in the vertebral fixation assembly in accordance with one or more embodiments.

FIG. 5A shows a perspective view of a side offset separator 510 that may be used as separators 260, 261. Side offset separator 510 includes an outer ring 518 (i.e., a ring member) that is attached to two side offsets 512, 514 that are separated by negative space. A lower edge 513 of side offset 512 and lower edge 515 of side offset 514 may be rounded to match the outer shape of rod members 130, 131 and thereby maximize the surface area contact between lower edges 513, 515 and rod members 130, 131. Side offset separator 510 includes an upper surface 522, and an inner surface 516. In some cases, a snap ring 520 is employed to secure side offset separator 510 to set screws 210, 211. In other cases, a snap ring is not used. FIGS. 5B-5C respectively show perspective and cross-sectional views of side offset separator 510 disposed in relation to set screw 210.

Figure 5D:
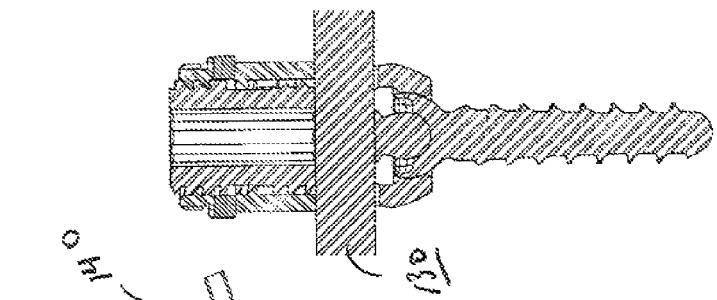
FIG. 5D is a cross-sectional view of one leg of the vertebral fixation assembly taken along the length of the incorporated rod after assembly using the side offset separator of FIG. 5A as the separator.
Figure 5E:
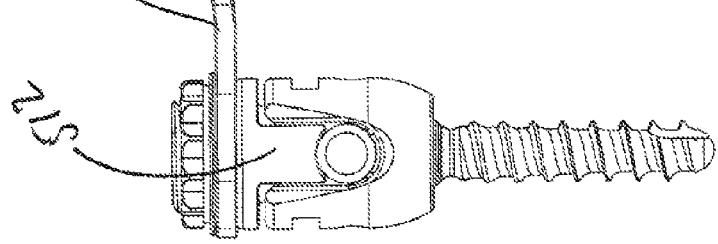
FIGS. 5E and 5G are a side view and a cross-sectional side view of the leg of the vertebral fixation assembly taken at a ninety degree rotation from the angle shown in FIG. 5D.
Figure 5G:
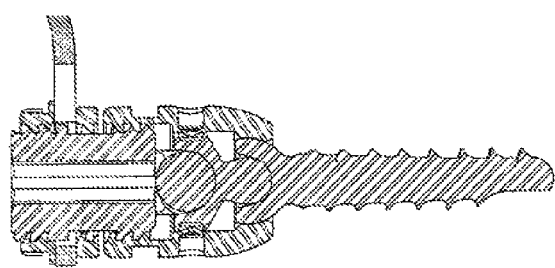

FIGS. 5D-5E are cross-sectional view and side views, respectively, of one leg of the vertebral fixation assembly 200 of FIG. 2 after assembly where side offset separator 510 is used as separator 260. In particular, FIG. 5D depicts a cross-section taken along a line 900 looking longitudinally to rod member 130 and axially to cross member 140; and FIG. 5E is a side view taken along a line 910 looking axially to rod member 130 and longitudinally to cross member 140. As shown, end 144 of cross member 140 is pressed against upper surface 522 of side offset separator 510, and lower edges 513, 515 of side offsets 512, 514 press against rod member 130 on either side of head 124. As lower edges 513, 515 fix the location of side offset separator 510 relative to head 124, a gap 590 may exist between upper edge 132 of head 124 when nut 150 is tightened. Side offsets 512, 514 extend into the negative space between sides 126, 128 of head 124. It should be noted that in other embodiments side offsets 512, 514 extend toward the surface of rod members without necessarily filling the negative spaces between sides 126, 128 of head 124.

In some cases, lower edges 513, 515 and/or upper surface 522 may be roughened to increase the amount of friction between upper surface 522 and cross member 140, and/or lower edges 513, 515 and the surface of rod member 130. Similar roughening may be applied to ends 144, 145 of cross member 140 and/or the lower surface of nuts 150, 151. Such roughening may be achieved by abrading or sandblasting the surface(s) of side offset separators 510, nuts 150, 151, upper edge 132 of head 124, upper edge 133 of head 125, the surface of rod members 130, 131, and/or ends 144, 145 of cross member 140. Based upon the disclosure provided herein one of ordinary skill in the art will recognize a variety of processes that may be employed to roughen the respective surfaces. FIG. 5F is a perspective view of the vertebral fixation assembly 200 using side offset separator 510 as the separator.

Where side offset separator 510 is disposed between cross member 140 and head 124, in some embodiments support for side offset separator 510 is derived from rod 130 and not directly from head 124, leaving a gap between head 124 and outer ring 518. By leaving a gap between outer ring 518 and head 124, transfer of torsional forces due to the contact between a lower surface of outer ring 518 and upper edge 132 may be reduced. Where there is some play between the lateral movement of rod member 130 and head 124, transfer of torsional force capable of undermining the installation of pedicle screw 120 is limited. In some embodiments, side offsets 512, 514 apply force directly to rod 130, which may provide increased locking forces for rod 130 compared to the use of only a single set screw engaging rod 130.

Figure 6:
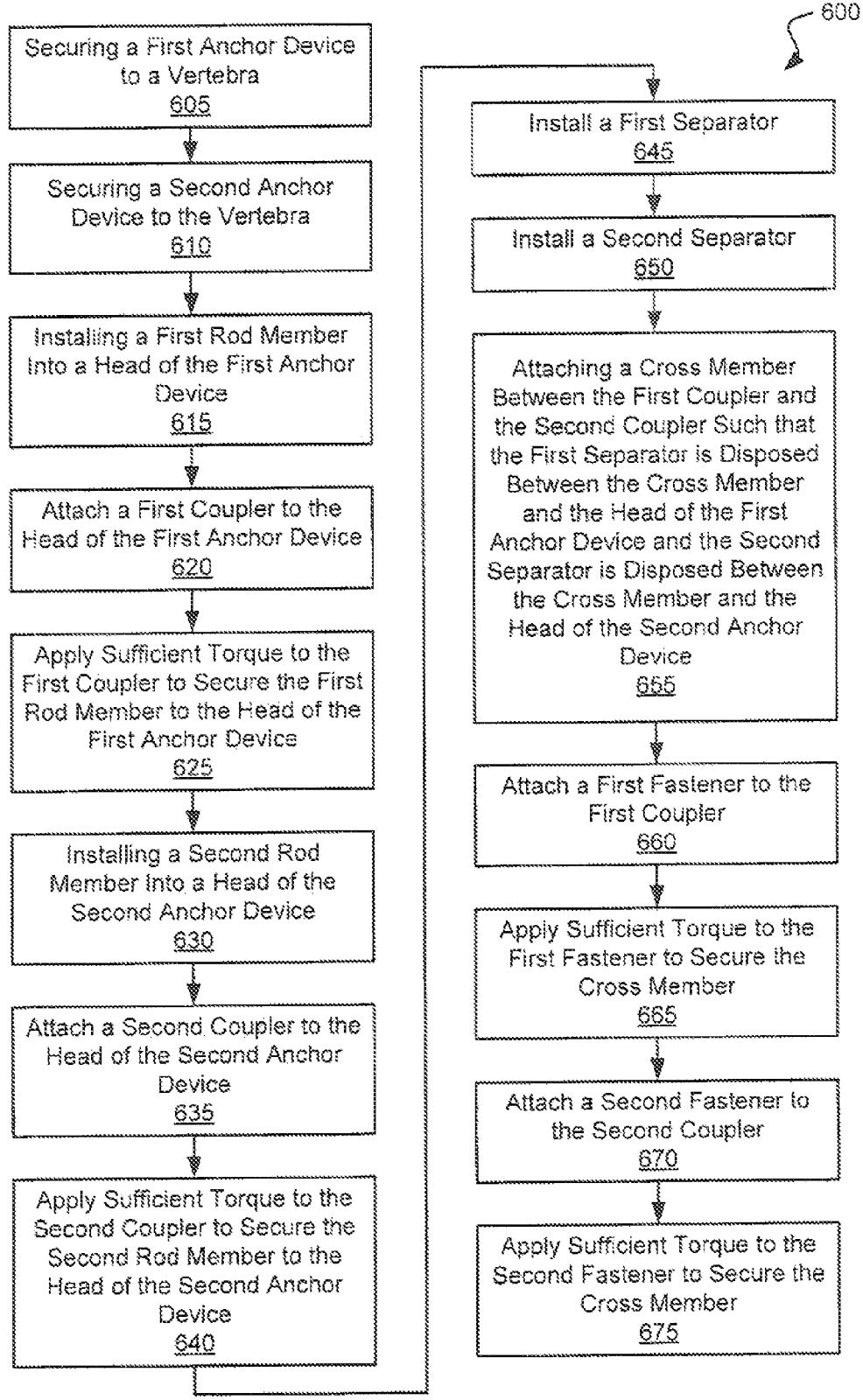
FIG. 6 is a flow diagram showing a method for installing a vertebral fixation system in accordance with various embodiments.

Turning to FIG. 6, a flow diagram 600 shows a method for installing a vertebral fixation system in accordance with various embodiments. Following flow diagram 600, a first anchor device is secured to a vertebra (block 605) and a second anchor device is secured to the vertebra (block 610). This may include, but is not limited to, screwing pedicle screws into opposite lateral sides of a vertebra. A first rod member is placed into the head of the first anchor device (block 615), and a first coupler is attached to the head of the first anchor device (block 620). Sufficient torque is then applied to the first coupler to secure the first rod member to the head of the first anchor device (block 625). A second rod member is placed into the head of the second anchor device (block 630), and a second coupler is attached to the head of the second anchor device (block 635). Sufficient torque is then applied to the second coupler to secure the second rod member to the head of the second anchor device (block 640). The aforementioned processes (blocks 615-640) may include sliding the respective rod member into the negative space between sides of the head of the respective anchor device followed by screwing a set screw into threads on an inner surface of the head of the respective anchor device. As the set screw is twisted into the head, a distal end of the set screw engages the rod member pressing it securely against the head of the respective anchor.

A first separator is installed in relation to the first coupler (block 645), and a second separator is installed in relation to the second coupler (block 650). Installation of the separators is modified depending upon the particular type of separator that is being installed. In particular, where the separator is integrated with the coupler as a single part, the installation process is accomplished by tightening the coupler into the head of an anchor device. Alternatively, where the separator is a nut, installing the separator includes threading the nut onto the coupler until it is moved to a desired location relative to the head of the anchor device. In some cases, the desired location is tight to the surface of the head of the anchor device. In other cases, the desired location is a distance away from the surface of the head of the anchor device. As another alternative where the separator is a washer, installing the separator includes sliding the washer over the coupler until it rests on the surface of the head of the anchor device. As yet another alternative, where the separator is a side offset separator installing the separator includes sliding the side offset separator over the coupler with the side offsets extending into the negative spaces between the sides of the head of the anchor device. Where a snap ring is used, the side offset separator may be pressed onto the coupler until the snap ring engages. In addition, it should be noted that other mechanisms may be used to secure the side offset separator to the associated coupler including, but not limited to, deformation of the outer ring, pinning, welding, or the like. In some embodiments, separators and couplers are preassembled. In other embodiments, separators and couplers are assembled just prior to use, or during use.

With the separators installed (blocks 645, 650), a cross member is installed between the first coupler and the second coupler such that the first separator is disposed between the cross member and the head of the first anchor device, and the second separator is disposed between the cross member and the head of the second anchor device (block 655). This may include sliding openings in the respective ends of the cross member over the corresponding first coupler and second coupler. A first fastener is then attached to the first coupler (block 660), and sufficient torque is applied to the first fastener to secure the cross member in place (block 665). Similarly, a second fastener is attached to the second coupler (block 670), and sufficient torque is applied to the second fastener to secure the cross member in place (block 675). Securing the aforementioned fasteners may include threading a nut onto the threads of the respective couplers.

In some cases, multiple instances of each of the elements of the described vertebral fixation systems are combined together in a kit. Such kits may include, but are not limited to, a number of anchor devices. The anchor devices may have different sizes, shapes, and/or engaging mechanisms. This allows an installer to select a particular anchor device depending upon the particular circumstance that is presented. Each of the anchor devices includes a head that is capable of mating to a coupler device and holding a cross member. A variety of rod members and cross members are also included in the kit. The rod members may include a number of rod members designed for seating in the head of an anchor device, and the cross members included may be designed for attachment between two couplers. A number of each type of rod and cross members including those of different lengths are included that allow an installer to assemble a desired vertebral fixation system. Also included are a number of couplers. In some cases, the couplers are all the same kind, while in other cases multiple different types of couplers are included such as, for example, set screws with continuous threads, set screws integrated with a separator, and/or set screws with an upper threaded region and lower threaded region may be included. Also included are a number of separators. In some cases, the separators are all the same type, while in other cases multiple different types of separators are included. Such separators may include, but are not limited to, nuts, washers, and/or side offset separators. The separators may comprise separate components, or may be pre-assembled into a complete coupler. The kit may be incorporated into a case that maintains all of the elements conveniently together. The case and included elements may be capable of insertion into an autoclave allowing for convenient sterilization.

In conclusion, various systems, devices, methods and arrangements for vertebral fixation are disclosed. While detailed descriptions of one or more embodiments have been provided above, various alternatives, modifications, and equivalents are possible. Therefore, the above description should not be taken as limiting the scope of possible embodiments, which is defined by the appended claims.

What is claimed is:

1. A vertebral fixation system, the system comprising:
    an anchor device, wherein the anchor device includes a head with an upper edge;
    a coupler having a first end and second end, wherein the first end is configured for attaching to the head and the second end is configured for attaching to a fastener;
    a cross member, wherein the cross member is configured for securing by the coupler between the head and the fastener; and
    a separator, wherein the separator is disposable between the upper edge of the head and the cross member;

wherein the separator and coupler are formed as a single part; and wherein the head has a head seat defined by a first head side separated from a second head side by a negative space, and wherein the system further comprises:

a rod member configured for placement in the head seat, wherein the coupler is further configured to secure the rod member to the head while maintaining a gap between the separator and the upper edge of the head.

2. The vertebral fixation system of claim 1, wherein the anchor device is a pedicle screw.

3. The vertebral fixation system of claim 1, wherein the head has a head seat defined by a first head side separated from a second head side by a first negative space and second negative space, and wherein the separator includes a first separator side configured to extend into the first negative space between the first head side and the second head side, and a second separator side configured to extend into the second negative space between the first head side and the second head side.

4. The vertebral fixation system of claim 3, wherein the head seat is configured to receive a rod member, and wherein the first separator side and the second separator side contact the rod member when the fastener is attached to the coupler.

5. The vertebral fixation system of claim 1, wherein the separator includes spaced apart first and second legs coupled to a ring member, the first and second legs configured to engage the rod member, and wherein the ring member is disposable between the cross member and the upper edge of the head.

6. The vertebral fixation system of claim 1, wherein at least a portion of a surface of the cross member is roughened.

7. The vertebral fixation system of claim 6, wherein the roughened surface of the cross member contacts the fastener when the fastener is attached to the coupler.

8. The vertebral fixation system of claim 6, wherein the roughened surface of the cross member contacts the separator when the fastener is attached to the coupler.

9. The vertebral fixation system of claim 1, wherein the coupler is a set screw having screw threads, wherein the fastener is a nut having nut threads configured to engage the screw heads, and wherein the head has an opening defined by a first head side separated from a second head side by a first negative space and a second negative space and the first head side and the second head side have head threads configured to engage the screw threads.

10. A vertebral fixation system, the system comprising:

an anchor device, wherein the anchor device includes a head with an upper edge;

a coupler having a first end and second end, wherein the first end is configured for attaching to the head and the second end is configured for attaching to a fastener;

a cross member, wherein the cross member is configured for securing by the coupler between the head and the fastener; and a separator, wherein the separator is disposable between the upper edge of the head and the cross member;

wherein the separator includes spaced apart first and second legs coupled to a ring member, the first and second legs configured to engage a rod member when the separator is coupled to the coupler, and wherein the ring member is disposable between the cross member and the upper edge of the head.

* * * * *